United States Patent [19]

Nishimura et al.

[11] Patent Number: 4,676,983
[45] Date of Patent: Jun. 30, 1987

[54] TUMOR CYTOSTATIC-CITOCIDAL FACTOR FROM BLOOD PLATELETS

[75] Inventors: Toyohiko Nishimura, Kobe; Hajime Hiratani, Sennan, both of Japan

[73] Assignee: Japan Chemical Research Co., Ltd., Kobe, Japan

[21] Appl. No.: 842,497

[22] Filed: Mar. 21, 1986

[30] Foreign Application Priority Data

Mar. 22, 1985 [JP] Japan .................................. 60-58789

[51] Int. Cl.$^4$ ............................................. A61K 35/14
[52] U.S. Cl. ........................................ 424/101; 514/2
[58] Field of Search ............................. 424/101; 514/2

[56] References Cited

PUBLICATIONS

Hara et al.–Chem. Abst. vol. 92 (1980), p. 196,061n.
Witkoski–Chem. Abst. vol. 97 (1982), p. 139,965q.

*Primary Examiner*—Sam Rosen
*Attorney, Agent, or Firm*—Burgess, Ryan & Wayne

[57] ABSTRACT

A tumor cytostatic-cytocidal factor is produced by disrupting platelets, extracting the disrupted platelets with an acidic aqueous solution or an acidic water-organic solvent mixture, and, after gel filtration, if desired, to separate a fraction having an estimated molecular weight of 10,000 to 20,000 and having tumor cell growth inhibiting activity, subjecting said extract or said fraction to chromatography to isolate a cytostatic fraction having a molecular weight of 10,000 to 20,000 and an isoelectric point of 9.0 to 10.0, giving a positive nihidrin reaction and being such that it is deactivated by trypsin but not deactivated by heating in physiological saline solution at 60° C. for 30 minutes or contacting at room temperature with 0.2N hydrochloric acid for 60 minutes or 70% formic acid for 30 minutes.

7 Claims, 8 Drawing Figures

TUMOR CYTOSTATIC-CITOCIDAL FACTOR FROM BLOOD PLATELETS

The present invention relates to a method of producing a novel substance which comprises recovering in high purity a tumor cytostatic-cytocidal factor which exists specifically in human and animal platelets.

There is available no failproof pharmacotherapy for tumors and despite the fact that many therapeutic drugs for tumors have been developed by many workers in various parts of the world, clinically the dominant therapy in use today is still a combination of surgical, radiation and drug treatments. Therapeutic agents for tumors are roughly classified into chemotherapeutic agents and immunosuppressive agents. Recently, however, many studies on biologically active substances occurring in platelets have been reported. Some representative studies are cited below.

Wasteson and others separated from platelets a platelet-derived growth factor having a molecular weight of 28,000 to 34,000 and a PI value of 9.0 to 11.0 and reported that the substance has the property to promote growth of smooth muscle cells, fibroblast cells and so on [Wasteson, Å et al: Biochem. J. 193, 907 (1981); Kenneday, B.B et al: J. B. C. 256, 8896 (1981)]. Lange et al separated from platelets a factor PBP (platelet basic protein) having a molecular weight of 11,000 to 15,000 and a PI value of 9.0 to 11.0 and claimed that PBP has the property to promote growth of Swiss 3T3 cells and so on [Lange, E. et al: Proc. Natl. Acad. Sci., USA, 77, 5914 (1980)]. Moreover, Castep et al obtained from platelets CTAP-III (connective tissue-activating peptide) [Castep, C. W. et al: Proc. Natl. Acad. Sci. USA, 80, 765 (1983)], Brown et al obtained PDECM (platelet-derived endothelial cell mitogen) [Brown, T. et al: Proc. Natl. Acad. Sci. USA, 80, 1641 (1983)], and Sporn et al obtained TGF-$\beta$ (transforming growth factor $\beta$-type) [Sporn, M. B. et al: J. B. C. 258, 7155 (1983)]. They found that all of these substances have activity to promote growth of various cells or analogous activity. However, it has not been reported that a substance which inhibits or kills human and animal tumor cells exists in a platelet extract.

As mentioned hereinbefore, chemotherapeutic agents for tumors which are used today are the so-called cytotoxis which manifest their effects by inhibiting growth of cells non-specifically and, as a consequence, they act on normal cells as well to cause very serious side effects such as leukopenia, sterility, alopecia, teratogenesis, carcinogenesis, and so on. Accordingly, strict limitations have been imposed on the dosages that can be administered. Furthermore, immunosuppressants for cancer do not directly inhibit tumor cells but produce therapeutic effects by acting on the defense mechanism of the body to thereby inhibit growth of tumors indirectly and, consequently, do not cause serious side effects as compared with chemotherapeutic aqents. However, as the defense mechanism of the body has been fairly much compromised in many tumor-bearing patients, the therapeutic effects obtainable with immunosuppressants are generally insufficient in comparison with chemotherapeutics.

The current status of therapeutic drugs for tumors being as described above, the development of an antitumor agent which would not cause serious side effects and which would act selectively upon tumor cells only has been awaited.

The present inventors conducted a comprehensive screening of blood-derived substances in regard to their influences on various animal cells and discovered in platelet extracts an active substance which acts specifically and directly on human and animal tumor cells produce growth-inhibiting or cytocidal effects but not cause any changes in normal cells at all. Further studies on this platelet-derived active substance led to the development of a method of producing a novel cytostatic-cytocidal factor against human animal tumor cells (hereinafter referred to as JR-8403). Thus, the platelets of various species of animals and humans were subjected to a repeated freeze-thaw cycle to disrupt the cells and granules and extracted with acidic water, and the extract was purified by gel filtration under acidic conditions. However the purification efficiency of this method was less than 10 times and no satisfactory results could be obtained. Therefore, the fraction obtained by the above technique was dialyzed, run onto a cation exchange resin and gradient elution with a neutral salt solution was attempted. The resultant purification efficiency was in excess of 100 times. Then, the active fraction from said cation exchange process was further subjected to reversed-phase chromatography on Synchropak RP-P (Synchrom, U.S.A.), an alkylated silica gel, MCI GEL CHP 20P (Mitsubishi Chemical Industries Ltd.), a high-porosity polystyrene. As a result, purification efficiency was increased to more than 1200 times. Then, the active fraction was further subjected to chromatofocusing (chromatographic electrofocusing) on a Mono P Prepack HR 5/20 column (Pharmacia). The above procedure resulted in a surprisingly high purification efficiency of more than 2000 times (Table 1). The present invention has been accomplished on the basis of the above findings.

The present invention relates to a method of producing a tumor cytostatic-cytocidal factor characterized by disrupting platelets, extracting the same with an acidic aqueous solution or an acidic water-organic solvent mixture, optionally followed by gel chromatography to separate a fraction containing tumor cell growth inhibiting activity having an estimated molecular weight of 10,000 to 20,000 and, then, subjecting said fraction to chromatography to isolate a fraction having tumor cell growth inhibiting activity which has a molecular weight of 10,000 to 20,000 and an isoelectric point of 9.0 to 10.0, gives a positive ninhydrin reaction and is deactivated by trypsin but not deactivated by heating in physiological salt solution at 60° C. over 30 minutes or upon contact with 0.2 N hydrochloric acid over 60 minutes or 70% formic acid over 30 minutes at room temperature.

While human platelets were used as the main material in the working examples of the invention, similar active substances may be found in the platelets of other warm-blooded animals including rodent, feline, canine, bovine and other species of animals and these active substances can also be employed in a like manner in the practice of the invention. Moreover, the marker cells used in the examples include human, rat and mouse cells, and the observed effects on these cells suggest that JR-8403 is a tumor cytostatic-cytocydal factor with little species-specificity.

JR-8403, which the present inventors obtained, is different from any of the substances heretofore extracted from platelets in various physicochemical and physiological properties and, therefore, is considered to be a novel bioactive substance. To isolate JR-8403, platelets are first disrupted by a repeated freeze-thaw cycle or by means of a homogenizer and the disrupted platelets are extracted with a solution of an inorganic or organic acid in water or in a mixture of water and an organic solvent. Preferred examples of such solvents include 1M-acetic acid, 1M-acetic acid-containing 50% ethanol and 0.1N-hydrochloric acid-containing 75% ethanol. JR-8403 can be extracted without deactivation by means of a somewhat strongly acidic aqueous medium or water-organic solvent system and in that case, the proteineous and other contaminants are removed. From the resulting extract, a clear extract can be obtained by the combined use of centrifugation and filtration through a filter with a pore size of the order of several $\mu$m. When the extract contains an organic solvent such as an alcohol, about 5 volumes of an equal-volume mixture of ether and ethanol is added, whereby the desired activity is precipitated. The precipitate is recovered by filtration and dissolved in acidic water. If desired, the extract may be subjected to gel filtration to obtain an active fraction. As the support material for gel filtration, Biogel P-60, P-100 (Bio-Rad Laboratories, U.S.A.), and Sephadex G-75 (Pharmacia Japan), etc. can be utilized.

The JR-8403 activity can be identified by the assay described hereinafter. The estimated molecular weight of this factor is 10,000 to 20,000. In accordance with the present invention, the above-mentioned extract or active fraction collected by gel filtration of the extract is subjected to at least one of ion exchange chromatography, reversed-phase chromatography and chromatofocusing to thereby separate the desired JR-8403 factor.

The ion exchange chromatography is carried out using a cation exchanger. The cation exchanger may be one of those based on natural or synthetic polymers and may for example be any of CM-Sephadex C-25 and SP-Sephadex Mono S (Pharmacia Japan), BIO.REX-70 (Bio-Rad Laboratories, U.S.A.) and so on. The acidic extract, either as it is or after gel filtration, is adjusted for pH and, then, run onto a column packed with the cation exchanger mentioned above, whereupon the JR-8403 activity is adsorbed on the cation exchanger. Then, gradient elution is carried out using an aqueous system of a neutral salt by the ascending method. The neutral salt may be any salt that is soluble and not cytotoxic, although sodium chloride is the most desirable.

Reversed-phase chromatography is carried out using a support having hydrophobic groups. Examples of such support include carbon chain-modified silica gels such as Synchropak RP-P Series (Synchrom, U.S.A.), and high-porality adsorbent polystyrene resins such as MCI.GEL CHP-20P Series (Mitsubishi Chemical Industries Ltd.), Amberlite XAD Series (Rohm and Haas, U.S.A.) and so on. Of these resins, the most preferred are Synchropak RP-P (C18), MCI.CHP 20P and amberlite XAD-7. The above-mentioned acidic extract, either as it is or after gel filtration, is applied to a column packed with said support, whereupon JR-8403 is adsorbed on the support. Then, gradient elution is carried out using a water-hydrophilic organic solvent system by the ascending method. The hydrophilic organic solvent includes lower aliphatic alcohols such as ethanol, propyl alcohol, etc., lower aliphatic ketones such as acetone, etc., and lower aliphatic nitriles such as acetonitrile, etc., for instance, and is preferably acetonitrile, methanol or isopropyl alcohol.

Chromatofocusing is carried out using a Mono P column in the FPLC system (Pharmacia Japan).

For example, with Poly-buffer 96 containing Pharmalyte 8-10.5 (both from Pharmacia Japan), a pH-gradient is constructed in the Mono P column and, then, elution is carried out isoelectrically. Of the chromatographic eluate obtainable by said ion exchange chromatography, reversed-phase chromatography or chromatofocusing, the active JR-8403 fractions detected by the assay described hereinafter are collected. Any of the above ion exchange chromatography, reversed-phase chromatography and chromatofocusing for purification of JR-8403 may be utilized alone or, preferably, in a combination of two or more.

The JR-8403 thus obtained is a white powder which gives a positive ninhydrin reaction, has a molecular weight of 10,000 to 20,000 (gel filtration) and gives single spot on SDS-electrophoresis. It is fairly stable against acids and heat and is deactivated by trypsin and pepsin.

Referring to the drawings, FIG. 1 is the elution curve of Sephadex G75 Super fine gel chromatograph (1M aqueous acetic acid) of Example 1;

Figure 7:
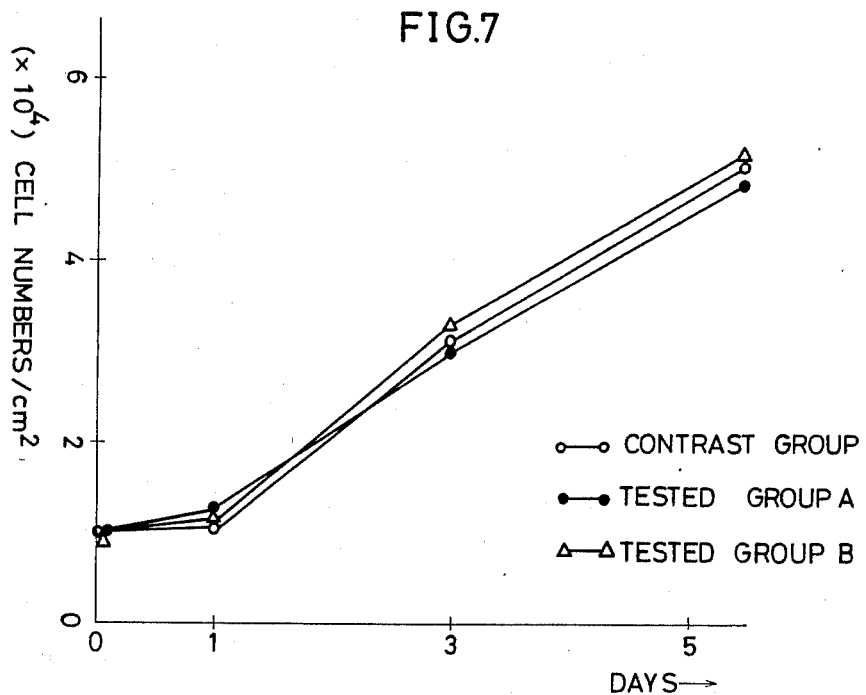
Figure 8:
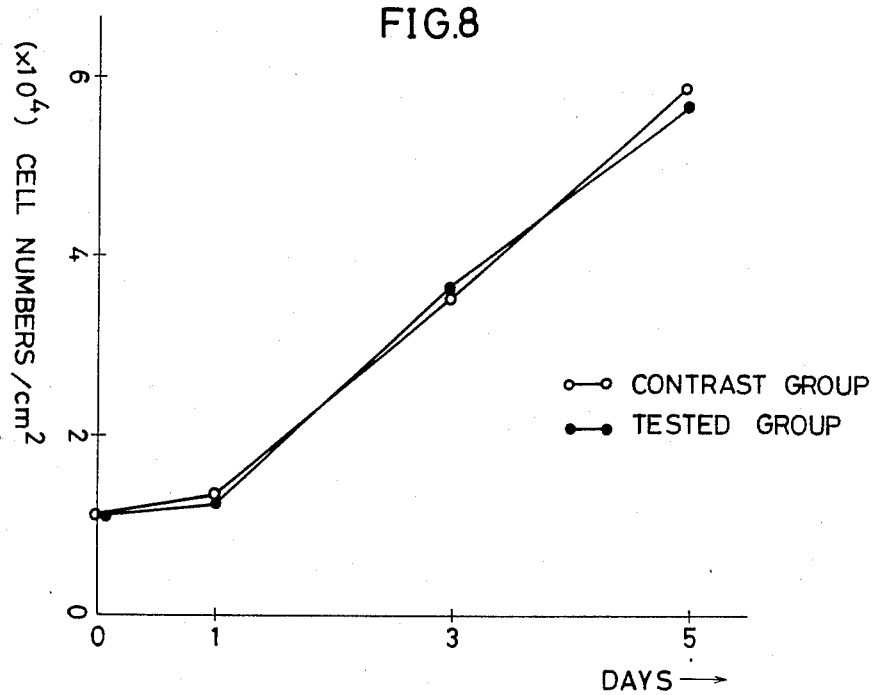

FIG. 7 shows the results of the activity assay (marker cells: primary culture of rat hepactocytes) of the factor of Example 4 (500 ng/ml) in Test Group A and the factor of Example 5 in Test Group B (500 ng/ml) against normal intact cells in Example 7; and FIG. 8 shows the results of the activity assay (marker cells: primary culture of chick embryonic cells) of the factor of Example 5 (1000 mg/ml) against normal cells.

The highly purified JR-8403 produced in accordance with the present invention has a potential to be an epoch making drug in the pharmacotherapeutic regimen for tumor- or cancer-bearing patients and can also be expected to enhance the defense function of the body which prevents degeneration of normal cells.

The following examples are intended to illustrate the invention in further detail and by no means be construed as limiting its scope.

EXAMPLE 1

Figure 1:
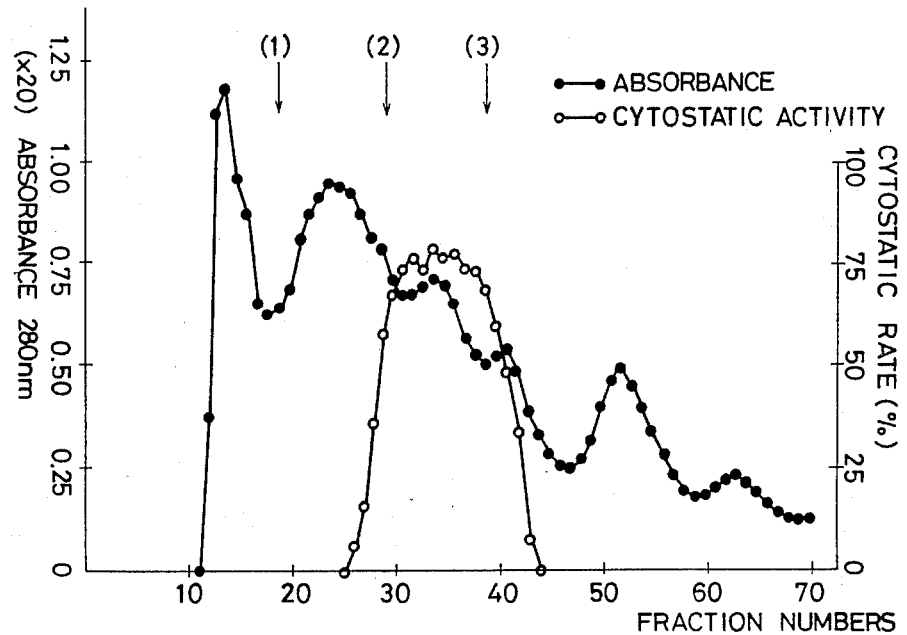

Platelets from 18 liters of fresh human blood were subjected to 2 freeze-thaw cycles and, then, 200 ml of a 1 M aqueous solution of acetic acid was added. The mixture was stirred for 1 hour and, then, centrifuged at 10,000 G for 45 minutes to remove insoluble matter, followed by lyophilization (1.58 g). To the resulting dry powder was added 20 ml of 1 M aqueous solution of acetic acid and the mixture was homogenized at room temperature. After 2 freeze-thaw cycles, the mixture was centrifuged at 12,000 G for 25 minutes to recover the supernatant. To the centrifugal sediment was added 5 ml of 1 M aqueous solution of acetic acid and the mixture was centrifuged. The resulting supernatant was combined with the first-mentioned supernatant. A column (3.6 cm×100 cm) was packed with Sephadex G-75 Superfine and after equilibration with 1 M aqueous solution of acetic acid, the above extract (pooled supernatant) was put on top of the resin and elution was carried out with 1 M aqueous solution of acetic acid by the descending method (flow rate 40 ml/hr., temperature 4° C.). The elution curve is shown in FIG. 1. In the diagram, the markers (1), (2) and (3) indicated by the arrowmark were all purchased from Pharmacia Japan (See the table below).

| No. | Marker | $Kav = \frac{Ve - Vo}{Vt - Vo}$ | M.W. |
|---|---|---|---|
| (1) | Ovalbumin (hen's egg) | 0.15 | 43,000 |
| (2) | Chymotrypsinogen A (bovine pancreas) | 0.26 | 25,000 |
| (3) | Ribonuclease A (bovine pancreas) | 0.4 | 13,700 |

JR-8403 activity was eluted at an estimated molecular weight of 10,000 to 20,000, and 275 ml of an active fraction was collected. This fraction was lyophilized to obtain 264.2 mg of dry powder. When a 10 μl portion of the active fraction was subjected to the JR-8403 activity assay described hereinafter, the marker tumor cells were significantly inhibited as compared with control.

EXAMPLE 2

Platelets from 5 liters of fresh bovine blood were subjected to 2 freeze-thaw cycles and 100 ml of a 75% aqueous solution of ethanol containing 0.1 N hydrochloric acid was added to the disrupted platelets. The mixture was stirred at 5° C. for 2 hours, after which it was centrifuged at 10,000 G for 40 minutes. To the supernatant was added 20 ml of 0.5 M-phosphate buffer (pH 5.5) and its pH was further adjusted to pH 5.5. The solution was allowed to stand at 5° C. for 2 hours and further centrifuged at 10,000 G and 5° C. for 60 minutes. To the supernatant was added 5 volumes of an equal-volume mixture of ether and ethanol and the whole mixture was allowed to stand at −20° C. over 2 nights. Then, the solution was centrifuged at 12,000 G and −20° C. for 60 minutes. The sediment was extracted with 1 M aqueous solution of acetic acid in the same manner as Example 1. In this manner, 12.5 ml of extract was obtained. A column (2.4 cm×100 cm) was packed with Sephadex G-75 Superfine and after equilibration with 1 M aqueous solution of acetic acid, the above extract was put on top of the resin and elution was carried out using 1 M aqueous solution of acetic acid by the descending method (flow rate 22.5 ml/hour, temperature 4° C.). JR-8403 activity was eluted at an estimated molecular weight of 10,000 to 20,000, and 180 ml of an active fraction was obtained. A 10 μl portion of this fraction was subjected to the JR-8403 assay described hereinafter. It was found that the marker tumor cells were significantly inhibited as compared with control.

EXAMPLE 3

The JR-8403 fraction (275 ml) prepared in Example 1 was subjected to salt interchange with YM-5 (Amicon) with a cut-off molecular weight of 5,000, followed by substitution with 0.02 M-phosphate buffer (pH 7.5) to a final volume of 245 ml. A column (3.2 cm×60 cm) was packed with CM-Sephadex C-25 (Pharmacia Japan) and after equilibration with 0.02 M phosphate buffer (pH 7.5), the above JR-8403 fraction was applied to the column to adsorb the activity. After the column was washed well with the same buffer, gradient elution was carried out with 0.02 M to 1 M aqueous solution of sodium chloride (flow rate 32 ml/hr., 4° C.).

Figure 2:
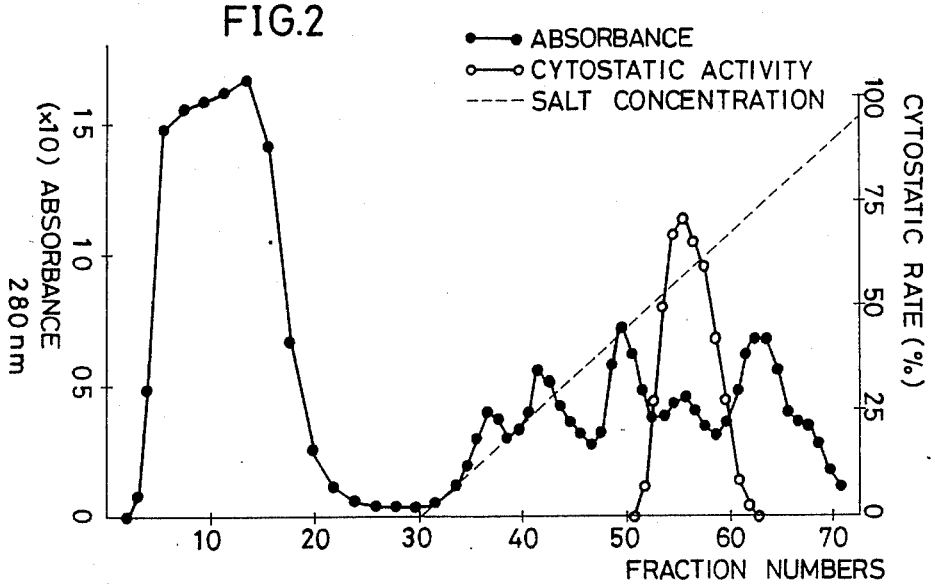
FIG. 2 is the elution curve of gradient elution chromatography using a CM-Sephadex C-25 column and a 0.02M-1M aqueous sodium chloride system in Example 3.

The elution curve is shown in FIG. 2. JR-8403 activity was eluted into the 0.6 to 0.9 M sodium chloride solution, so that 128.5 ml of an active fraction was collected. This fraction was lyophilized to give 14.6 mg of dry powder. When a 10 μl portion of the above eluate was subjected to the JR-8403 assay, it inhibited the marker tumor cells significantly.

EXAMPLE 4

Figure 3:
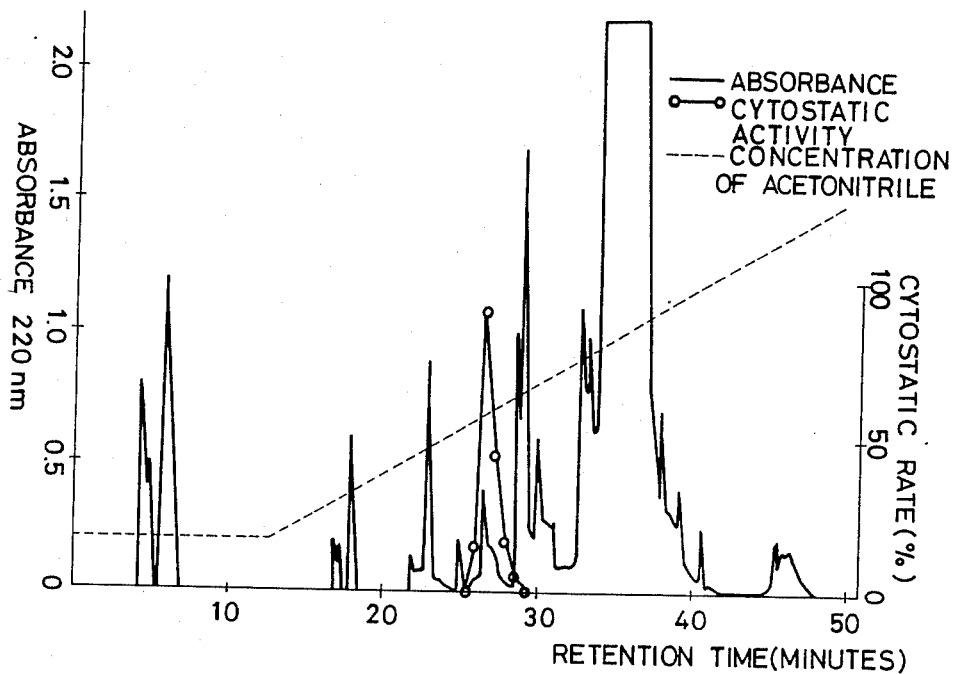
FIG. 3 is the elution curve of high performance liquid chromatography using an alkyl ($C_{18}$)modified silica gel (Silica Gel Synchropak RP-P) and a 0-75% acetonitrile (in 0.05% aqueous trifluoroacetic acid) system of Example 4.

The lyophilized powder of JR-8403 (14.6 mg) obtained in Example 3 was added to 10 ml of a 0.05% aqueous solution of trifluoroacetic acid and homogenized at room temperature using a homogenizer. The homogenate was subjected to a freeze-thaw cycle and centrifuged at 12,000 G for 30 minutes to give a supernatant. The centrifugal sediment was washed with 2 ml of a 0.05% aqueous solution of trifluoroacetic acid and centrifuged, and the resulting supernatant was combined with the first-mentioned supernatant. A high-performance liquid chromatography system (Gilson) was fitted with a column (10.0 mm×250 mm) of Synchropak RP-P, silica gel carrying alkyl ($C_{18}$) groups, and after equilibration with 0.05% aqueous trifluoroacetic acid, 4 ml of the above supernatant was passed. After the column was washed with 0.05% aqueous trifluoroacetic acid, the adsorbed activity was eluted with 0 to 75% solution of acetonitrile in the same solvent as above by the gradient elution method. The elution curve is shown in FIG. 3.

JR-8403 activity was eluted into 40–60% acetonitrile. This columnwise purification procedure was repeated 3 times and the active fractions obtained from 12 ml of extract were combined and lyophilized to give 1.2 mg of dry white powder. This powder was dissolved in 5.0 ml of physiological saline solution and 10 μl of its 100-fold dilution was subjected to the JR-8403 assay. The product of this example was found to cause a significant growth inhibition of marker tumor cells as compared with control.

EXAMPLE 5

Of 5 ml of the JR-8403 fraction obtained in Example 4, 1 ml was subjected to chromatofocusing (Pharmacia). A Mono P Prepack HR 5/20 Column (Pharmacia) was set on the FRLC (Pharmacia) and the JR-8403 fraction was adsorbed. Then, using Pharmalyte 8–10.5 (Pharmacia), pH-gradient elution was carried out between pH 8 and 10.5. JR-8403 activity was eluted between pH 9 and 10, and 3.5 ml of an active fraction was obtained. This active fraction was dialyzed against physiological saline solution across a dialysis membrane with a cut-off molecular weight of 3,500 over 2 nights and the dialysate was lyophilyzed. The above procedure was repeated for a total of 5 times and 0.7 mg of white powder was obtained from 5 ml of the JR-8403 fraction of Example 4. This product had a molecular weight of 10,000 to 20,000 (FIG. 1) and an isoelectric point of 9.0 to 10.0

Figure 4:
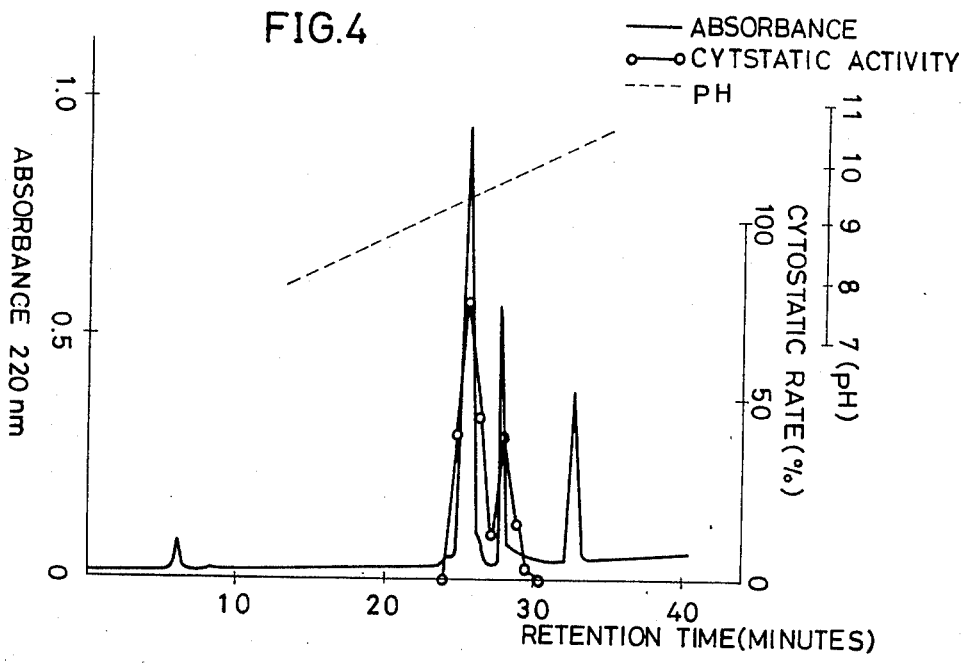
FIG. 4 is the elution curve of pH gradient elution chromatography using Pharmalyte 8-10.5 in Example 5.

(FIG. 4), and gave a positive ninhydrin reaction, and its tumor cytostatic activity was not deactivated by heating in physiological salt solution at 60° C. over 30 minutes or at 100° C. over 1 minute or upon contact with 0.2 N-hydrochloric acid over 60 minutes or 70% formic acid over 30 minutes at room temperature. Incidentally, when this product was treated with 0.1 mg/ml of trypsin (derived from bovine pancreas, Difco) at 37° C. for 24 hours, it was almost completely deactivated.

EXAMPLE 6

Action of JR-8403 on tumor cells

Figure 5:
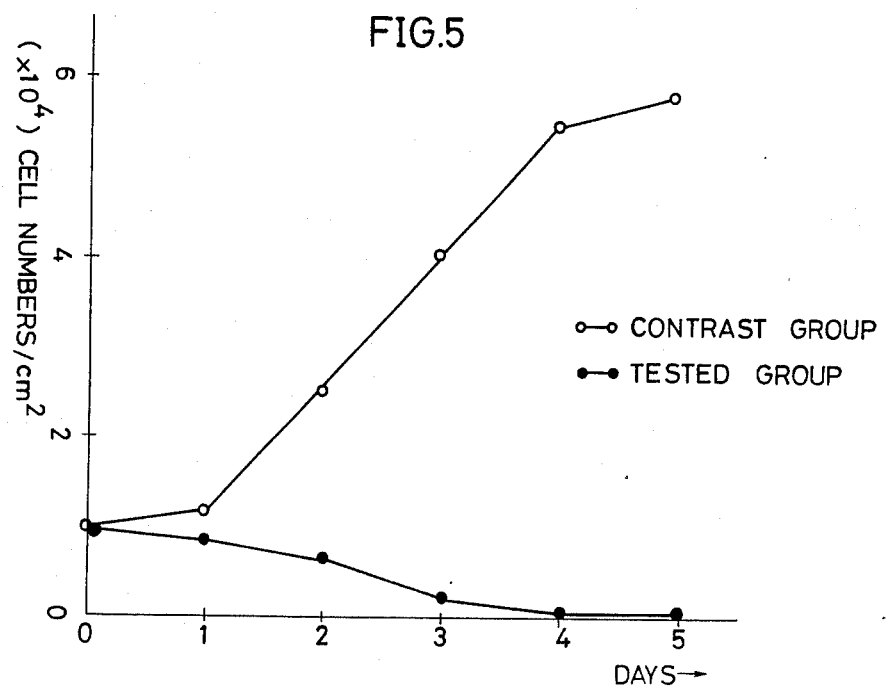
FIG. 5 shows the results of the activity assay (marker cells: KB) of the factor of Example 5 (200 ng/ml medium) in Example 6.
Figure 6:
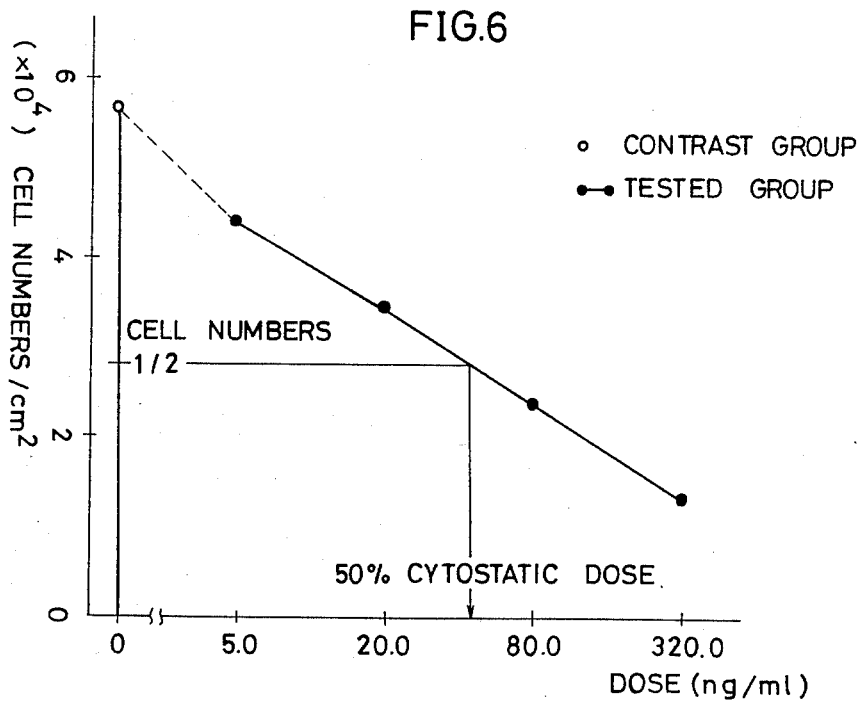
FIG. 6 is the dose-activity curve (marker cells: HeLa) constructed by varying the dosage of the same factor in Example 6.

Tumor cells, namely KB cells (human rhinopharyngeal cancer), HEP-2 cells (human laryngeal cancer), HeLa cells (human cervical cancer), G-361 cells (human malignant melanoma), K-562 cells (human leukemia), L-1210 cells (mouse leukemia) and L-929 (mouse connective tissue cancer) were respectively cultured for 48 hours. Then, 1 ml of 10% bovine serum-containing Eagle's medium was inoculated with $10^4$ cells of each and incubated in 5% carbon dioxide streams at 37° C. for 5 days. Control groups without addition of the test factor and test groups to which the JR-8403 of Example 5 (200 ng/ml medium) was added were concurrently cultured and in each group the viable cells not stained by Trypan Blue were counted under the light microscope at 24-hour intervals. Typical results are shown in FIG. 5. Similar experiments were carried out by varying the addition level of JR-8403 and a dose-response curve was constructed. An example is shown in FIG. 6. The 50% cytostatic concentrations against various tumor cells are given in Table 2.

EXAMPLE 7

Action of JR-8403 on normal cells

Normal cells, namely Flow 7000 cells (human fetal foreskin), primary culture of rat hepatocytes, primary culture of calf kidney cells, and primary culture of chick whole embryonic cells, were subjected to at least 2 serial passages and $10^4$ cells of each were added to 1 ml aliquots of 10% bovine serum-containing Eagle's medium. In 3 groups, namely the groups to which the JR-8403 of Example 4 was added and the groups to which the JR-8403 of Example 5 was added, plus control groups, culture was conducted in 5% carbon dioxide gas streams at 37° C. for 5 days. On day 1, 3 and 5, the viable cells not stained by Trypan Blue were counted under the light microscope. Against the baseline cell count in the control group, the cytostatic effect of the JR-8403 sample was evaluated. The results are set forth in Table 3. FIG. 7 shows the results obtained using the primary culture of rat hepatocytes as marker cells in Test Group A using the JR-8403 of Example 4 (500 ng/ml) and Test Group B using the JR-8403 of Example 5 (500 ng/ml). Similarly, FIG. 8 shows the results obtained by using the primary culture of chick whole embryonic cells as marker cells and the JR-8403 of Example 5 (1000 mg/ml) as the test substance.

Method for Assay of JR-8403 Activity

As marker tumor cells, either KB cells (human pharyngeal cancer) or HEp-2 cells (human laryngeal cancer) are used. The medium is 10% bovine serum-containing Eagle's medium (0.1% non-essential amino acid added, manufactured by Dainippon Pharmaceutical Co., Ltd.). The medium is put in a multi-dish tray (Nunc, Denmark) and a suspension of $10^4$ marker cells is added, followed by addition of a solution of the test substance in physiological saline. To a control group, the same volume of physiological saline only is added. In an open system, culture is conducted in a 5% $CO_2$ gas stream at 37° C. under 100% humidity. The culture is continued for 3 to 4 days and the time course is monitored. When cells in the control group have grown sufficiently, trypsin treatment and Trypan Blue staining are carried out and the unstained viable cells are counted under the light microscope. The ratio of the number of viable cells in the test group to that in the control group is used to calculate the 50% cytostatic dose.

TABLE 1

| Example No. | Dry weight of JR-8403 fraction from 18 l human blood | Purification efficiency (times) | Dose which produces 50% cytostatic effect (per ml medium) |
|---|---|---|---|
| 1 | 1580 mg | 1 | (—) |
| 1 | 264.2 mg | 6.0 | 115.0 μg |
| 3 | 14.6 mg | 108.2 | 1.2 μg |
| 4 | 1.2 mg | 1316.7 | 80 ng |
| 5 | 0.7 mg | 2257.1 | 45 ng |

TABLE 2

| Tumor cell line | | 50% Cytostatic concentration of the JR-8403 of Example 5, dry weight per ml medium |
|---|---|---|
| Name | Origin | |
| KB | Human | 40 ng |
| HEp-2 | Human | 85 ng |
| HeLa | Human | 45 ng |
| G-361 | Human | 35 ng |
| LA-4 | Mouse | 65 ng |
| K-562 | Human | 50 ng |
| L-1210 | Mouse | 85 ng |
| L-929 | Mouse | 45 ng |

TABLE 3

| Normal cell line | | 50% Cytostatic concentration of the JR-8403 of Example 5, dry weight per ml medium |
|---|---|---|
| Name | Origin | |
| Flow 7000 | Human | >1,800 ng |
| Primary culture of rat hepatocytes | Rat | 2,500 ng |
| Primary culture of calf kidney cells | Calf | >10,000 ng |
| Primary culture of chick embryonic cells | Chick | >10,000 ng |

We claim:

1. A method of producing a tumor cytostatic-cytocidal factor characterized by disrupting platelets, extracting the disrupted platelets with an acidic aqueous solution or an acidic water-organic solvent mixture, and either directly thereafter or after gel filtration separating a fraction having an estimated molecular weight of 10,000 to 20,000 and having tumor cell growth inhibiting activity, subjecting said extract or said fraction as the case may be to chromatography to isolate a cytostatic fraction having a molecular weight of 10,000 to 20,000 and an isoelectric point of 9.0 to 10.0, giving a positive ninhydrin reaction and being such that it is deactivated by trypsin but is not deactivated by heating in physiological saline solution at 60° C. for 30 minutes or contacting at room temperature with 0.2 N hydrochloric acid for 60 minutes or 70% formic acid for 30 minutes.

2. A method as set forth in claim 1 wherein said gel chromatography is performed under acidic to neutral conditions.

3. A method as set forth in claim 1 wherein said chromatography is (1) ion exchange chromatography which comprises adsorbing the activity on a cation exchanger and, then, carrying out gradient elution with an aqueous solution system of a neutral salt, (2) reversed-phase chromatography which comprises adsorbing said activity on a support carrying hydrophobic groups and, then, carying out gradient elution using a hydrophilic neutral organic solvent system or (3) chromatofocusing which comprises adsorbing said activity on a cation exchanger and, then, carrying out elution isoelectrically using a pH-gradient eluant system or a combination of two or more of the chromatographic procedures.

4. A tumor cytostatic-cytocidal factor prepared by the method of claim 1.

5. A tumor cytostatic-cytocidal factor obtained from blood platelet extract, having a molecular weight of from 10,000 to 20,000 as determined by gel filtration, an isoelectric point of 9.0 to 10.0, which factor gives a positive ninhydrin reaction, and which is deactivated by trypsin but not deactivated by heating in physiological salt solution at 60° C. over 30 minutes or upon contact with 0.2 N hydrochloric acid over 60 minutes or 70% formic acid over 30 minutes at room temperature.

6. A pharmaceutical composition useful for the treatment of tumors comprised of an anti-tumor effective amount cytostatic-cytocidal factor of claim 5, and a pharmaceutically acceptable carrier.

7. A method of producing an anti-tumor affect comprising administering to tumor cells an effective amount of the pharmaceutical composition of claim 6.

* * * * *